(12) United States Patent
Lee et al.

(10) Patent No.: US 6,951,718 B1
(45) Date of Patent: Oct. 4, 2005

(54) **RPOB GENE FRAGMENTS AND A METHOD FOR THE DIAGNOSIS AND IDENTIFICATION OF *MYCOBACTERIUM TUBERCULOSIS* AND NON-TUBERCULOSIS MYCOBACTERIAL STRAINS**

(75) Inventors: Hyeyoung Lee, No. 190-1106, Woosung APT., Yangjae-1-dong, Seocho-ku, Seoul (KR); Young Kil Park, Seongnam-si (KR); Gill-Han Bai, Seongnam-si (KR); Sang-Jae Kim, Seoul (KR); Sang-Nae Cho, No. 310-103, Seonsoochon APT., 89, Banglee-dong, Songpa-ku, Seoul (KR); Yeun Kim, Pajoo-si (KR); Hee Jung Park, Seoul (KR)

(73) Assignees: Sang-Nae Cho, Seoul (KR); Hyeyoung Lee, Kangwon-do (KR)

( * ) Notice: Subject to any disclaimer, the term of this patent is extended or adjusted under 35 U.S.C. 154(b) by 546 days.

(21) Appl. No.: 09/697,123

(22) Filed: Oct. 27, 2000

(30) Foreign Application Priority Data

Oct. 27, 1999 (KR) ........................ 1999-46795

(51) Int. Cl.[7] ............................ C12Q 1/68; C12Q 1/44; C07H 21/04; C12P 19/34; C12N 1/20
(52) U.S. Cl. ............................ 435/6; 436/19; 436/91.2; 436/253.1; 536/23.1; 536/23.2; 536/23.7; 536/24.32; 536/24.33
(58) Field of Search .................... 435/6, 19, 91.2, 435/253.1; 536/23.1, 23.2, 24.32, 24.33, 23.7; 356/344

(56) References Cited

U.S. PATENT DOCUMENTS 6,242,584 B1 * 6/2001 Kook et al. ............. 536/23.1
2002/0187467 A1 * 12/2002 Gingeras et al. ............. 435/6

OTHER PUBLICATIONS

Lee, H. et al. Species identification of mycobacteria by PCR–restriction fragment length polymorphism of the rpoB gene. Journal Clinical Microbiology 38(8):2966–2971 (Aug. 2000).*

Talenti, A. et al. Rapid identification of mycobacteria to the species level by polymerase chain reaction and restriction enzyme analysis. Journal of Clinical Microbiology 31(2):175–178 (Feb. 1993).*

Abed, Y., Bollet, and P. de Micco. 1995. Demonstration of *Mycobacterium kansasii* species heterogeneity by the amplification of the 16S–23S spacer region. J. Med Microbiol. 43:156–158.

Avaniss–Aghajani, E., K. Jones, A. Holtzman, T. Aronson, N. Glover, M. Bolan, S. Froman, and C. F. Brunk. 1996. Molecular technique for rapid identification of mycobacteria. J. Clin. Microbial. 34:98–102.

Boddinghaus, B., T. Flohr, H. Blocker, and E. C. Bottger. 1990. Detection and identification of mycobacteria by amplification of rRNA. J. Clin. Microbiol. 28:1751–1759.

Bosne, S., and V. Levy–Frebault. 1992. Micobactin analysis as an aid for the identification and *Mycobacterium fortuitum* and *Mycobacterium chelonae* subspecies. J. Clin. Microbiol. 30:1225–1231.

Butler, W. R., K. C. Jost, Jr., and J. O. Kilburn 1991. Identification of mycobacteria by high–performance liquid chromatography. J. Clin. Microbiol. 29:2468–2472.

Corpet. F. 1988. Multiple sequence alignment with hierachical clustering Nucl. Acids. Res. 16:10881–10890.

(Continued)

Primary Examiner—Carla J. Myers
Assistant Examiner—Diana Johannsen
(74) Attorney, Agent, or Firm—Nixon & Vanderhye, P.C.

(57) ABSTRACT

The present invention is related to rpoB gene fragments and method for the diagnosis and identification of *Mycobacterium tuberculosis* and non-lubercuolsis Mycobacterial strains using rpoB gene and it's fragments.

3 Claims, 11 Drawing Sheets

OTHER PUBLICATIONS

Devallois A., K. S. Goh, and N. Rastogi. 1997. Rapid identification of mycobacteria species and proposition of an algorithm to differentiate 34 mybobacterial species to species level by PCR–RFLP analysis of the hsp65 gene. J. Clin. Microbiol. 35:2969–2973.

Fiss, E., F. Chehab, and G. Brooks. 1992. DNA amplification and reverse dot blot hybridization for detection and identification of mycobacteria to the species level in the clinical laboratory. J. Clin. Microbiol. 30:1220–1224.

Fries, J., R. Patel, W. Piessen, and D. Wirth. 1990. Genus and species–specific DNA probes to identify mycobacteria using the polymerase chain reaction. Mol. Cell. Probes. 4:87–105.

Gingeras, T. R., G. Ghandour, E. Wang, A. Berno, P. M. Small, Drobniewski, D. Alland, E. Desmond, M. Holoknly, and J. Drenkow, 1998. Simultaneous genotyping and species identification using hybridization patter recognition analysisi of generic Mycombacterium DNA arrays. Genome Res. 8:435–448.

Hance, A. J., B. Grandchamp, V. Levy–Frebault, D. Lecossier, J. Rauzier, D. Bocart, and B. Gicquel. 1989. Detection and identification of mycobacteria by amplification of mycobacterial DNA. Mol. Microbiol. 3:843–849.

Hetherington, S. V., A. S. Watson, and C. C. Patrick. 1995. Sequence and analysis of the rpoB gene of *Mycobacterium smegmatis*. Antimicrob. Agents Chemother. 39:2164–2166.

Honore, N. T., S. Bergh, S. Chanteau, F. Doucet–Populaire, K. Eiglmeier, T. Garnier, C. Georges, P. Launois, T. Limpaiboon, S. Newton, K. Niang, P. Del Portillo, G. R. Ramesh, P. Reddi, P. R. Ridel, N. Sittisombut, S. Wu–Hunter, and S. T. Cole. 1993. Nucleotide sequence of the first cosmid from the *Mycobacterium leprae* genome project: structure and function of the Rif–Str regions. Mol. Microbiol. 7:207–214.

Hughes, M. S., R. A. Skuce, L.–A. Beck, and S. D. Neill. 1993. Identification of mycobacteria from animals by restriction enzyme analysis and direct DNA cycle sequencing of polymerase chain reaction–amplified 16S rRNA gene sequences. J. Clin. Microbiol. 31:3216–3222.

Kapur, V., L–L. Li, M. R. Hamrick, B. B. Plikaytis, T. M. Shinnick, A. Telenti, W. R. Jacobs, A. Banerjee, S. Cole, K. Y. Yuen, J. E. Clarridge, B. N. Kreswirth, and J. M. Musser. 1995. Rapid Mycobacterium species assignment and unambiguous identification of mutations associated with antimicrobial resistance in *Mycobacterium tuberculosis* by automated DNA sequencing. Arch. Pathol. Lab. Med. 119:131–138.

Kim, B.–J., S.–H. Lee, M.–A. Lyu, S.–J. Kim, G.–H. Bai, S.–J. Kim, G.–T. Chae, E.–C. Kim, C.–Y. Cha, and Y.–H. Kook. 1999. Identification of Mycobacterial species by comparative sequence analysis of the RNA polymerase gene (rpoB). J. Clin. Micro. 37:1714–1720.

Kirschner, P., B. Springer, U. Vogel, A. Meier, A. Wrede, M. Kiekenbeck, F.–C. Bange, and E. C. Bottger. 1993. Genotypic identification of Mycobacteria by nucleic acid sequence determination: report of 2–year experience in a clinical laboratory. J. Clin. Micorbiol. 31:2882–2889.

Kusunoki, S., T. Ezaki, M. Tamesada, Y. Hatanka, K. Asano, Y. Hashimoto, and E. Yabuuchi, 1991. Application of colorimetric microdilution plate hybridization for rapid genetic identification of 22 mycobacterium species. 29:1596–1603.

Levey–Frebault V., M. Daffe, K. S. Goh, M.–A. Laneelle, C. Asselineau and H. L. David. 1983. Identification of Mycobacterium species. J. Clin. Microbiol. 29:1596–1603.

Mabilat, C., S. Desvarenne, G. Panteix, N. Machabert, M.–H. Bernillon, G. Guardiola, and P. Cros. 1994. Routine identification of *Mycobacterium fortuitum* and *Mycobacterium chelonei*. J. Clin. Microbiol. 32:2702–2705.

Marks, J., and T. Szulga. 1965. Thin–layer chromatography of mycobacterial lipids as an aid to classification; technical procedures; *Mycobacterium fortuitum*. Tubercle 46:400–411.

Miller, L. P., J. T. Crawford, and T. M. Shinnick. 1994. The rpoB gene of *Mycobacterium tuberculosis*. Antimicrob. Agents Chemother. 38:805–811.

Musial, C., L. Tice, L. Stockman, and G. Roberts. 1988. Identification of mycobacteria from culture by using the Gen–probe rapid diagnostic system for *Mycobacterium avium* complex and *Mycobacterium tuberculosis* complex. J. Clin. Microbiol. 26:2120–2123.

Picardeau, M., G. Prod'hom, L. Raskine, M. P. LePennec, and V. Vincent, 1997. Genotypic characterization of five subspecies of *Mycobacterium kansasii*. J. Clin. Microbiol. 35:25–32.

B. D. Plikaytis, M. A. Yakrus, W. R. Butler C. L. Woodley, V. A. Silcox, and T. M. Shinnick, 1992. Differentiation of slowly growing Mycobacterium species, including *Mycobacterium tuberculosis*, by gene amplification and restriction fragment length polymorphism analysis. J. Clin. Microbiol. 30:1815–1822.

Rogall, T., T. Flohr, and E. Bottger. 1990 Differentiation of Mycobacterium species by direct sequencing of amplified DNA. J. Gen Microbiol. 136:1915–1920.

Ross, B. C., K. Jackson, M. Yang, A. Sievers, and B. Dwyer. 1992. Identification of genetically distinct subspecies of *Mycobacterium kansasii*. J. Clin. Microbiol. 30:2930–2933.

Shinners, D. and H. Yeager, Jr. 1999. Nontuberculous Mycobacterial infection. Clinical syndromes and diagnosis: overview p341–350. In D. Schlossberg (ed.), Tuberculosis and nontuberculous mycobacterial infection $4^{th}$ ed. W. B. Sunders Co., Philadelphis. PA.

Shinnick. 1987, The 65–Kilodalton Antigen of *Mycobacterium tuberculosis*. J. Bacteriol. 169:1080–1088.

Shinnick, T. M., M. H . Vodkin, and J. C. Williams. 1988 The *Mycobacterium tuberculosis* 65–Kilodlton antigen is a heat shock protein which corresponds to common antigen and to the *Escherichia coli* GroEL protein. Infect Immun. 56:446–451.

Soini, H., E. C. Bottger, and M. K. Viljanen 1994 Identification of Mycobacteria by PCR–Based sequence determination of the 32–Kilodalton protein gene. J. Clin. Microbiol. 32:2944–2947.

Springer, B., L. Stockman, K. Teschner, G. D. Roberts, and E. C. Bottger. 1996. Two–laboratory collaborative study on identification of Mycobacteria: molecular versus phenotypic methods. J. Clin. Microbiol. 34:296–303.

Takewaki, S.–I., K. Okuzumi, I. Manabe, M. Tanimura, K. Miyamura, K.–I. Nakahara, Y. Yazaki, A. Ohkubo, and R. Nagai. 1994. Nucleotide sequence comparison of the Mycobacterial dnaJ gene and PCR–restriction fragment length polymorphisim analysis for identification of Mycobacterial species. Int. J. Syst. Bacteriol44:159–166.

Taylor, T. B., C. Patterson, Y. Hale and W. W. Safranek. 1997. Routine use of PCR–restriction fragment length polymorphism analysis for identification of Mycobacteria growing in liquid media. J. . Clin. Microbiol. 35:79–85.

Telenti, A., F. Marchesi, M. Balz, F. Bally, E. C. Bottger, and Bodmer. 1993. Rapid identification of Mycobacteria to the species level by polymerase chain reaction and restriction enzyme analysis. Rapid identification of mycobacteria to the species level by polymerase chain reaction and restriction enzyme analysis. J. Clin Microbiol. 31:175–178.

Tsang, A., I. Drupa, M. Goldgerg, J. McClatchy, and P. Brennan. 1983. Use of serology and thin–layer chromatography for the assembly of an authenticated collection of serovars within the *Mycobacterium avium–Mycobacterium intracellulare–Mycobacterium scrofulaceum* complex.

Vaneechoutte, M., H. D. Beenhouwer, G. Claeys, G. Vershraegen, A. D. Rouk, N. Paepe, A. Elaichouni, and F. Portaels. 1993. Identification of Mycobacterium species by using amplified ribosomal DNA restriction analysis. J. Clin. Microbiol. 31:2061–2065.

\* cited by examiner

Figure 4

| Msp I | Strains | Hae III | Other enzymes |
|---|---|---|---|
| 190 ─── | ► M. gastri | 180/105 | |
| ├─175 ─── | ► M. smegmatis | 200/90/50 | |
| ├─150 ── 95 ── 80 ── 40 ─ | ► N. nova | 250/50 | |
| ├─ 90 ── 80 ── 60 ─── | ► R. equi | 200/95 | |
| ├─ 80 ── 70 ── 60 ─── | ► M. kansasii type II | 210/100 | |
| └─ 60 ── 40 ─── | ► M. kansasii type III | → 210/100 | |
|  | └► M. kansasii type IV | → 180/130 | |
| 175 ─── | ► M. gallinarum | 200/90 | |
| ├─140 ─── | ► M. celatum type II | 210/95/90 | |
| ├─100 ── 80 ─── | ► M. intracellulare | 180/90 | |
| │      ├─ 70 ─── | ► M. fortuitum type I | 120/90/80 | |
| │      └─ 40 ─── | ► M. gordonae type III | 300 | |
| ├─ 90 ─── | ► M. austroafricanum | 200/90 | *Sau* 3A1 |
| ├─ 80 ── 60 ── 40 ─── | ► TB/M. bovis | ┌► 250/100 | → 250/70 |
| │                     └► M. africanum | └► 250/100 | → 165/90/70 |
| └─ 40 ─── | ► M. szulgai | → 200/115 | |
|  | └► M. gordonae type IV | → 270 | |
| ├─ 70 ── 60 ── 40 ─── | ► M. kansasii type V | 175/55/50 | |
| └─ 60 ── 40 ── 30 ─── | ► M. kansasii type I | 205/90 | |
| 145 ┌─110 ── 95 ──45 ─── | ► M. xenopi | 300 | |
| ├─ 95 ┌─ 80 ─── | ► N. brasiliense | 150/90/80 | *Kpn* I |
| │      ├─ 45 ── 35 ─── | ► M. celatum type I | ┌► 210/95/90 | → 175/185 |
| │      └─ 40 ── 30 ─── | ► M. gordonae type I | └► 210/95/90 | → 360 |
| └─ 80 ── 40 ─── | ► M. gordonae type II | 330 | |
| 110 ┌─ 70 ── 60 ──50 ─── | ► M. malmoense | 190/75 | |
| └─ 55 ── 50 ── 40 ─── | ► M. terrae | 195/60 | |
| 105 ┌─ 95 ── 80 ┌─ 70 ─── | ► M. fortuitum type II | → 120/90/80 | → |
| │               ├► M. simiae | → 180/110 | → |
| │               └► M. genavense | → 150/100 | *Bst* EII |
| │      ┌─45 ─── | ► M. abscessus | ┌► 130/100/90 | → 145/95 |
| │      └─40 ─── | ► M. chelonae | └► 130/100/90 | → 225/145 |
| ├─ 90 ── 70 ── 60 ─── | ► M. ulcerans | 210/80/65 | |
| └─ 80 ┌─ 70 ──40 ─── | ► M. asiaticum | 290 | |
|       └─ 45 ──40 ─── | ► M. avium | 270 | |
| 100 ┌─ 95 ┌─ 90 ──80 ─── | ► M. flavescens | 200/85/50 | |
| │         └─ 65 ─── | ► M. thermoresistibile | 200/85 | |
| ├─ 90 ── 70 ┌─── | ► M. phlei | 210/90 | |
| │            └─── | ► M. moriokaense | 200/90 | |
| │      └─ 50 ──40 ─── | ► M. pulveris | 250/90 | |
| ├─ 70 ── 60 ─── | ► M. haemophilum | 290 | |
| └─ 60 ── 40 ─── | ► M. marinum | 200/80 | |
| 90 ── 70 ── 65 ── 50 ──40 ─── | ► M. scrofulaceum | 210/125 | |

```
        160       170       180       190       200       210       220       230   235
----+----+---------+---------+---------+---------+---------+---------+---------+---------+----|
C--------------GAGGGTCAGCAC----ACGATG-ACGTTCCGGCGGGACCGAGGTTCCGGTGAGACCGACGACAT  (SEQ ID NO:  4)
C--------------GAGGGTCAGCAC----ACGATGACCGTCCCGGCGGCGGCCGAGGTGCCGGTTGAGACCGACGACAT (SEQ ID NO:  1)
C--------------GAGGGTCAGCAC----ACGATGACCGTCCCGGCGGCGGCCGAGGTGCCGGTTCCGGTGAGACCGACGACAT (SEQ ID NO:  3)
C--------------GAGGGTCAGCAC----ACGATGACCGTCCCGGCGGCGGCCGAGGTGCCGGTGAGACCGACGACAT (SEQ ID NO:  2)
C--------------GAGGGTCAGTCG----GCGATGACGGTTCCCGGCGGCGGCCGAGGTGCCGGTGAGACCGACGACAT (SEQ ID NO: 15)
C--------------GAGGGTCAGCCC----ACGATGACCGTCCCGGCGGCATCGAGGTGCCGGTCGAGACCGACGACAT (SEQ ID NO: 10)
C--------------GAGGGCCAGACC----GCGATGACCGCTCCGGCGGTGTCGAGGTGTCGAGGTGCCGGTCGAGACCGACGACAT (SEQ ID NO: 11)
C--------------GAGGGCCAGACC----GCGATGACCGCTCCGGCGGTGTCGAGGTGTCGAGGTGCCGGTCGAGACCGACGACAT (SEQ ID NO: 19)
C--------------GAGGGCCAGACC----GCGATGACCGCTCCGGCGGCGTCGAGGTCCGAGGTGCCGGTCGAGACCGACGACAT (SEQ ID NO: 12)
C--------------GAGGGCCAGACC----ACGATGACCGTTCCGGCGGCGTCCACCGAGGTGCCGGTGCCGGTGGAGACCGACGACAT (SEQ ID NO: 20)
C--------------GAGGGCCAGCCC----ACGATGACCGTCC---CGGCATCGAGGTGCCGGTCGAGGTGCCGGTGGAAACCGACGACAT (SEQ ID NO:  5)
C--------------GAGGGTCAGACC----ACGATGACCGTTCCGGCGGCGGGGGGTCGAGGTGCCGAGGTGCCGGTGGAAACCGACGACAT (SEQ ID NO: 16)
C--------------GAGGGTCAGACC----ACGATGATCGTCGTTCCGGCGGCCGAGGTGCCGAGGTGCCGGTGGAAACCGACGACAT (SEQ ID NO: 22)
C--------------GAGGGCCAGGCC----ACGATGACCGTCCCGGGGCGGAGTCGCGTGCCGAGGTGCCGGTGGAAACCGACGACAT (SEQ ID NO:  8)
T--------------GAGGGTCAGTCG----ACGATGACCGTTCAGTGCGTGGCGGCCGAGGTGCCGAGTGATACTGACGACAT (SEQ ID NO: 17)
C--------------GAGGGCCAGGCA----ACGATGACCGTTCCGGCGGCGTCGAGGTGCCGAGGTGCCGGTGGAGACCGACGACAT (SEQ ID NO: 23)
C--------------GAGGGGCACGCC----ACGATGAAGTCCCGCCCCCCCCGGGCGGCCTCGAGGTCCCGAGGTCGGTGGAGACCGACGACAT (SEQ ID NO: 14)
C--------------GAGGGCCAGACC----ACGATGACCGTCCCGCCCCCCGGCGGCGTGAGGTGAGGTGCCGGTCGAGGTCGACGACAT (SEQ ID NO: 24)
C--------------GAGGGCCAGACC----ACGATGACCGTCCCGGCGGCGTCCGTGAGGTCGAGGTGCCGGTCGAGGTGATGACGACAT (SEQ ID NO:  7)
C--------------GAGGGCCAGACC----ACGATGACCGTCCCGGCGGCGTGAGGTGAGGTGCCGGTCGAGGTGATGACGACAT (SEQ ID NO: 21)
T--------------CAGGGCCAGACAAG----ACGATGACCGTCATGACTGCTGCCGCCCCCGGCGGCATCGAGGTCGAGGTGAAACCGACGACAT (SEQ ID NO: 18)
CCACGCCCGTACGGATGGCCAGCCCGCCGTCATGACTGCTGCCGCCCCCCCGGCGGCATCGAGGTCGAGGTGAAACCGACGACAT (SEQ ID NO:  9)
CCACGCCCTCTCAGGGTGGCCAGCCCGCCGCCCCCCCGGCGGCGTCGAGGTCGAGGTGAAACCGACGACAT (SEQ ID NO: 13)
c              GAgGGcCAg cc     aCgATGAccgtcCCcGgCGgcgt cGAGGTgCCgGTgGAgaccGACGACAT
```

| 1 | 2 | 3 | 4 | 5 | 6 |
|---|---|---|---|---|---|
| ● |   |   |   |   |   |
| 7 | 8 | 9 | 10 | 11 | 12 |
| B● | 14 | 15 | 16 | 17 | 18● |
| 19 | 20 | 21 | 22 | 23 | 24 |
| 25 | 26 | 27 | 28 | 29 | 30 |
| 31 | 32 | 33 | 34 | 35 | 36 |
| 37 | 38 | 39 | 40 | 41 | 42 |
| 43 | 44 | 45 | 46 | 47 | 48● |

Figure 7b

| 1 | 2 | 3 | 4 | 5 | 6 |
|---|---|---|---|---|---|
|   | ● |   |   |   |   |
| 7 | 8 | 9 | 10 | 11 | 12 |
| B | 14 | 15 | 16 | 17 | 18● |
| 19 | 20 | 21 | 22 | 23 | 24 |
| 25 | 26 | 27 | 28 | 29 | 30 |
| 31 | 32 | 33 | 34 | 35 | 36 |
| 37 | 38 | 39 | 40 | 41 | 42 |
| 43 | 44 | 45 | 46 | 47 | 48 |

*Figure 7c*

| 1 | 2 | 3 | 4 | 5 | 6 |
|---|---|---|---|---|---|
| 7 | 8 | 9 | 10 | 11 | 12 |
| B | 14 | 15 | 16 | 17 | 18 |
| 19 | 20 | 21 | 22 | 23 | 24 |
| 25 | 26 | 27 | 28 | 29 | 30 |
| 31 | 32 | 33 | 34 | 35 | 36 |
| 37 | 38 | 39 | 40 | 41 | 42 |
| 43 | 44 | 45 | 46 | 47 | 48 |

US 6,951,718 B1

RPOB GENE FRAGMENTS AND A METHOD FOR THE DIAGNOSIS AND IDENTIFICATION OF *MYCOBACTERIUM TUBERCULOSIS* AND NON-TUBERCULOSIS MYCOBACTERIAL STRAINS

FIELD OF THE INVENTION

The present invention is related to rpoB gene fragments and a method for the diagnosis and identification of *Mycobacterium tuberculosis* and non-tuberculosis Mycobacterial strains using rpoB gene fragments.

BACKGROUND OF THE INVENTION

Since the early 1980s) there has been a increase in disease caused by organisms called nontuberculous mycobacteria (NTM), which is the generic name for mycobacteria other than *M. tuberculosis* and *M. leprae* (MOTT). They affect both immune-competent and immune-compromised persons, and patients with the human immunodeficiency virus (HIV) are known to be especially vulnerable. The most frequent NTMs involved in disease cases are known to be *M. avium, M. intracellulare, M. scrofulaceum, M. kansasii, M. fortuitum* complex, *M. chelonae, M. abscessus, M. szulgai, M. malmoense, M. marinum, M. ulcerans,* and *M. africanum, M. bovis* (28). Clinical diagnosis and treatment of nontuberculous mycobacterial infections are an increasingly frequent challenge to clinicians.

Currently, clinical diagnosis of mycobacteria to the species level is primarily based on cultural and biochemical tests. These conventional tests take several weeks, and the tests sometimes fail precise identification. The procedures for these tests are complex, laborious, and are usually impeded by the slow growth of mycobacteria in clinical laboratories. Additional methods, such as high-performance liquid chromatography, gas-liquid chromatography, thin-layer chromatography (5,21 36), and DNA sequencing analysis (3, 4, 15, 16, 17, 19, 26, 31, 32) can differentiate mycobacteria to the species level, but these are labor-intensive and difficult to perform for routine use in many clinical laboratories.

In contrast to the above-mentioned techniques, recent molecular techniques employing PCR-amplified products offers an easy, rapid, and inexpensive way to identify several mycobacterial species in a single experiment. PCR-restriction fragment length polymorphism analysis (PRA) has been developed to target mycobacterial genes, which are present in all mycobacteria such as hsp65 (7, 11, 25, 29, 30, 34, 35), 16S rRNA (2, 14, 37), and dnaJ (33). However, these techniques are still cumbersome since they require several enzyme digestions for species identification, and the results are not easy to interpret for species identification due to the limited size variation of DNA fragments after digestion.

On the other hand, probe-hybridization technique which employs DNA of the clinical specimen and oligo-probe hybridization (8, 9, 10, 18, 20, 23) is a useful tool for direct and rapid identification of NTM species. However, commercial kits currently available in the market are very expensive, limited only to 5 mycobacterial species, and the identification of a single species requires an independent experiment.

SUMMARY OF THE INVENTION

The present invention provides DNA ts including sequence SEQ. ID. NO. 1 to 4 and 6 to 24.

The present invention provides a method of identification of Mycobacterium strain comprising the step of 1) digesting a DNA fragment which has one of the sequence Seq. ID NO 1 to 4 to 24 with resriction enzyme to obtain DNA fragment length polymorphism pattern; 2) isolating DNA fragment from microorganism to identify; 3) amplifying said DNA fragment; 4) digesting said amplified DNA fragment with the same restriction enzyme in step 1); 5) obtaining DNA fragment length polymorphism pattern from DNA fragment in step 4); and 6) comparing DNA fragment length polymorphism pattern from step 1) with DNA fragment length polymorphism pattern from step 5).

Preferably, said restriction enzymes are enzyme HaeIII, MspI, Sau3Al or BstEII.

Preferably, the DNA fragment length polymorphism pattern from steps 1) and 5) is obtained by electrophoresis.

And the Mycrobacteria strain to be identified by this method are preferably *M. tuberculosis, M. avium, M. absessus, M. flavescence, M. africanum, M. bovis, M.chelonae, M. celatum, M. fortuium, M.gordonae, M.gastri, M. haemophilum, M.intraecllulare, M. kansasii, M. malmoense, M. marinum, M. szulgai, M. terrae, M. scrolaceum, M. ulcerans* or *M. xenopii.*

BRIEF DESCRIPTION OF THE DRAWINGS

FIG. 4. An algorithm was constructed based on the results of PRA with 40 mycobacterial reference strains and 3 other related bacterial strains. The PRA results of 10 other mycobacterial reference strains listed in this figure to make the algorithm concise.

FIG. 7A-C. Examples of PCR-dot blot hybridization experiments. A total of 48 PCR products generated by using primers, RPO5, and RPO3', and DNAs from 48 mycobacterial species were blotted on the membrane, and an oligonucleotide probe which is specific to a certain mycobacterial species was hybridized at conditions described in the Materials and Methods section. Blotted DNAs on the membrane were as following; 1; *M. tuberculosis*, 2: *M. scrofulaceum* 3: *M. szulgai*, 4: *M. gastri*, 5: *M. kansasii* type I, 6: *M. Kansasii* type II, 7. *M. kansasii* type III, 8: *M. kansasii* type IV, 9: *M. kansasii* type V, 10: *M. terrae*, 11: *M. avium*, 12: *M. intracellularae*, 13: *M. africanum*, 14: *M. celatum* type I, 15: *M. celatum* type II, 16: *M. haemophilum*, 17: *M. malmoense*, 18: *M. bovis*, 19: *M. chelonae*, 20: *M. abscessus*, 21: *M. ulcerans*, 22: *M. marinum*, 23: *M. genevanse*, 24: *M. simiane*, 25: *M. flavescens*, 26: *M. fortuitum* type I, 27: *M. fortuitum* type II, 28: *M. peregrinum*, 29: *M. triviale*, 30: *M. phlei*, 31: *M. parafortuitum*, 32: *M. vaccae*, 33: *M. aurum*, 34: *M. neoaurum*, 35: *M. fallax*, 36: *M. xenopi*, 37: *M. aichiense*, 38: *M. mucogenicum*, 39: *M. nonchromogenicum*, 40: *M. senegalense*, 41: *M. smegmatis*, 42: *M. thermoresistable*, 43: *M. intermedium*, 44: *M. gordonae* type I, 45: *M. gordonae* type IL, 46: *M. gordonae* type II, 47: *M. gordonae* type IV, 48: *M. bovis*, BCG.

DETAILED DESCRIPTION OF THE INVENTION

Mycobacterial identification to the species level is not only of academic interest but also is important because it provides a great deal of useful information on the epidemiology and pathogenesis of the organism, suggesting potential intervention strategies including successful treatment of patients on the clinical base. It is therefore important to develop methods that are rapid and simple, but yet precise and cost-effective to be used in a wide variety of clinical laboratories around the world. Currently available methods for differentiation of mycobacteria to the species level are time-consuming evaluations using phenotypic and biochemical tests or laborious procedures using expensive equipment.

As compared to other molecular methods, the PRA method certainly fits these requirements better. It is rapid and precise since it employs PCR, and simple and cost-effective since it does not require any expensive equipment or laborious processes and can differentiate numerous species of mycobacteria within a single experiment. Owing to these advantages, several PRA methods based on different genes of mycobacteria have been developed (2, 7, 11, 14, 25, 29, 30, 33, 34, 35, 37). However, most of those methods require use of more than two enzymes to differentiate mycobacteria at the species level, and require computer-assisted software program to differentiate restriction fragments since the profiles of certain mycobacterial species were not distinctive enough for bare-eye interpretation.

Figure 1A:
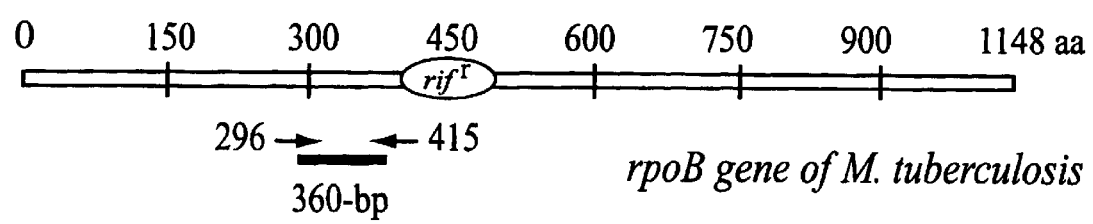
FIG. 1. (A). A diagram showing amplified region of the rpoB for PRA in this study. The primers PRO5' and RPO3' generates 360-bp PCR product, which locates upstream of rif' region associated with resistance of *M. tuberculosis* to rifampin. (B). An agarose gel (2%) with 360-bp PCR products using PRO5' and RPO3'. Lane M. DNA size marker (100-bp ladder), lane 1: negative control (no DNA sample), lanes 2–11: PCR products with reference strains of mycobacteria.
Figure 1B:
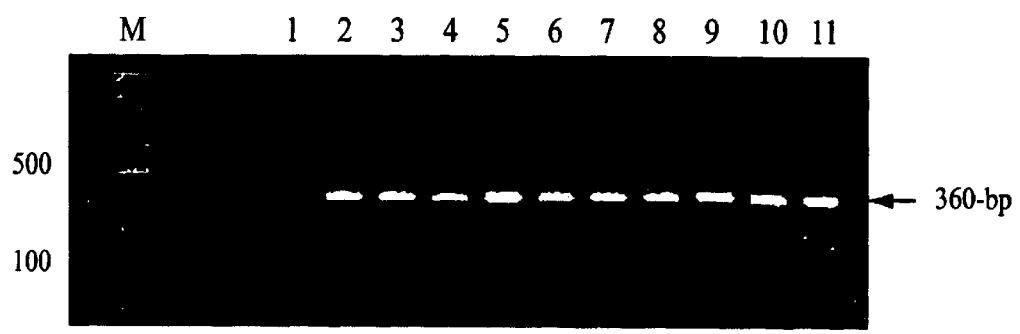

The new PRA method developed through this invention has more advantages that the previous ones. As presented in FIG. 1, it is apparent that most of the species harbor unique PRA profiles. Unlike other PRA profiles, which may need computer-assisted analysis and interpretation of the gels, we do not face problems in resolving all the patterns obtained during the experiments. Furthermore, problems including gel-to-gel variations or confusion with the size of the restriction fragments were limited with the use of 50-bp size marker and PRA profile of *M. bovis* as an internal size marker.

On the other hand, the four members of the *M. tuberculosis* complex that are difficult to separate by using other methods such as sequence analysis or HPLC of mycolic acids were also undistinguishable by PRA method, confirming that they do belong to a genetically similar group. However, unlike other methods, this new PRA method can further differentiate *M. africanum* from other *M. tuberculosis* complex by Sau 3AI digestion. Therefore, in case the clinical isolate shows the *M. tuberculosis* complex profiles, PCR products can be further processed to differentiate *M. africanum* from other *M. tuberculosis* complex by Sau 3AI digestion. In addition, *M. tuberculosis* and *M. bovis* can be differentiated by PCR amplification using esat-6 gene derived PCR primers, which is known to be present only in the genome of *M. tuberculosis*.

Currently in our laboratory, a substantial number of mycobacterial clinical isolates have now been identified by our new PRA method in parallel with other reference methods, including conventional tests and molecular biological methods such as PRA based on hsp65 gene and sequence analysis based on the rpoB gene. As a conclusion of this experiment, it is certain that this new PRA is a rapid, cost-effective, and efficient method for the identification of mycobacteria in a clinical microbiology laboratory. The whole procedure can be done in 2 days when culture is used. PRA has been successful when using a loopful of culture taken from solid media or using 100 $\mu$l taken from liquid culture such as MGIT for mycobacterial species identification. Both of systems work well even with genomic DNA simply boiled for 5 min.

In addition to the PRA, PCR-dot blot and PCR-reverse dot blot hybridization method employing oligonucleotide probes that are highly specific to each mycobacterial species were also shown to be valuable techniques for simple and rapid identification of mycobacterial species. The oligonucleotides developed in this study were highly species-specific, thus indicating a usefulness of these probes in development of mycobacterial identification system which can be useful in clinical settings.

To develop new molecular techniques that are easier and more precise for mycobacterial species identification than currently available ones, we chose the rpoB gene that encodes $\beta$ subunit of RNA polymerase. The information-rich nature of the rpoB gene has been recently employed in differentiation of mycobacteria by DNA hybridization array (10) or by DNA sequence analysis (16). However, the rpoB region used in these previous studies has limited sequence variation that can be used for species identification of mycobacteria. In the present study, we extended the genetic knowledge of the rpoB gene to the highly polymorphic region that is suitable for developing mycobacterial species identification system using molecular biological techniques such as PRA and PCR-DNA hybridization. We also chose this region of the rpoB gene to be flanked by highly conserved sequences, thus can be suitable for PCR amplification of the rpoB region of all mycobacterial species using the same set of PCR primers.

In this study, 50 reference strains representing 44 different mycobacterial species and 6 subspecies were used to amplify the 360-bp region of the rpoB gene. The PCR products were then subjected to restriction fragment length polymorphism analysis (RFLP) to determine the efficacy of this region of the rpoB gene for mycobacterial species identification using PRA method. Subsequently, on the basis of PRA profiles generated with reference strains, an algorithm was generated, and a total of 260 clinical isolates were evaluated using new PRA method. In brief, the results clearly showed that this novel PRA method based on the rpoB gene generates clear and distinctive results for easy, rapid, and precise identification of mycobacterial species that can be employed in clinical laboratories for prompt and accurate diagnosis.

Subsequently, PCR amplified regions of the rpoB gene derived from 30 mycobacterial species that are known to have clinical importance were sequenced. In brief, results of sequence analysis showed that in the region of rpoB we amplified, highly polymorphic and species-specific regions exist, and thus indicated the usefulness of these regions for developing a new PCR-dot blot hybridization technique. On the basis of these sequence information, species-specific oligo-probes were designed and used to establish mycobacterial species identification system using DNA hybridization techniques such as PCR-dot blot and PCR-reverse blot hybridization method.

The restriction analysis of a 360-bp fragment within rpoB gene after single Msp I digestion is highly effective for differentiating most of mycobacteria even at the species level. Only several species require additional enzyme digestion such as Hae III, Sau 3AI, Hinc II, etc. For some species, such as *M. gordonae, M. kansasii, M. fortuitum,* and *M. celatum,* the discrimination was even obtained at the subtype level. For *M. kansasii,* this subdivision was clearly linked to genetic divergence observed previously by other investigators (1, 24, 27). It is therefore possible that using this PRA method, the discrimination at a subgroup level for other species could be similarly linked to bacteriological and clinical specificities.

Therefore, this invention provide a rpoB gene fragment (SEQ. ID. NO. 1 to 4 and 6 to 24) which has conserved sequence and polymorphic sequence between mycobacterial species.

Also this invention provide a method for diagnosis and identification of Mycobacterium tuberculosis and Non-tuberculosis Mycobacterium strain comprising the step of 1) digesting a DNA fragment which has one of the sequence Seq. ID. NO 1 to 24 with restriction enzyme to obtain DNA fragment length polymorphism pattern;
2) isolating DNA fragment from microorganism to identify;
3) amplifying said DNA fragment using primer (SEQ. ID. NO.25 and 26);
4) digesting said amplified DNA fragment with the same restriction enzyme in step 1);
5) obtaining DNA fragment length polymorphism pattern from DNA fragment in step 4); and
6) comparing DNA fragment length polymorphism pattern from step 1) with DNA fragment length polymorphism pattern from step 5).

Preferably, said restriction enzymes are enzyme HaeIII, MspI, Sau3Al or BstEII.

Preferably, the DNA fragment length polymorphism pattern from steps 1) and 5) is obtained by electrophoresis.

And the Mycrobacteria strain to be identified by this method are listed in Table 1.

Though the present invention has been described with regard to its preferred embodiments, one skilled in the art will appreciate from a reading of this disclosure that various changes in form and detail can be made without departing from the scope and spirit of the invention.

EXAMPLES

Materials and Methods

Mycobacterial samples.

A total of 50 mycobacterial reference strains representing 44 mycobacterial species and 3 related species which belong to 2 different genera (Table 1) were used to develop the new PRA method in this study. Among them, 40 mycobacterial strains and 3 related species were obtained from the Korean Institute of Tuberculosis (KIT) and the Korean National Tuberculosis Association (KNTA) in Seoul, Korea. Four species were obtained from the Korean Collection for Type Cultures (KCTC) at the Korean Research Institute of Bioscience & Biotechnology (KRIBB) and *M. abscessus,* which was recently separated from *M. chelonae* as an independent new species, was obtained from Department of Clinical Pathology at Yonsei University Medical College (YUMC). Five subtypes of *M. kansasii* were generously given by Dr. V. Vincent in the Laboratoire de Référence des Mycobactéries, Institut Pasteur in France.

Clinical isolates subjected for PRA to evaluate the new method were obtained from KIT. All clinical isolates used in this study were identified on the basis of conventional tests that include microbiological characteristics and biochemical tests. For some cases, strains were subjected for conventional PRA method based on hsp65 gene (7,35) to help precise identification of clinical isolates.

TABLE 1

Bacterial strains used in this study

| | Species | Strain | Source |
|---|---|---|---|
| 1 | *M. abcessus* | Pettenkofer Inst. | YUMC |
| 2 | *M. africanum* | ATCC 25420 | KIT |
| 3 | *M. arcinogens* | ATCC 35753 | KIT |
| 4 | *M. asiaticum* | ATCC 25276 | KIT |
| 5 | *M. aurum* | ATCC 23366 | KIT |
| 6 | *M. austroafricanum* | ATCC 33464 | KRIBB |
| 7 | *M. avium* | ATCC 25291 | KIT |
| 8 | *M. bovis* | ATCC 19210 | KIT |
| 9 | *M. bovis* BCG | French Strain 1173P2 | KIT |
| 10 | *M. celatum* type I/II | ATCC 51130/ATCC 51131 | KIT |
| 11 | *M. chelonae* | ATCC 35749 | KIT |
| 12 | *M. chitae* | ATCC 19627 | KIT |
| 13 | *M. fallax* | ATCC 35219 | KIT |
| 14 | *M. fortuitum* type I/II | ATCC 6841/ATCC 49404 | KIT |
| 15 | *M. gallinarum* | ATCC 19710 | KRIBB |
| 16 | *M. gastri* | ATCC 15754 | KIT |
| 17 | *M. genavense* | ATCC 51233 | KIT |
| 18 | *M. gilvum* | ATCC 43909 | KIT |
| 19 | *M. gordonae* | ATCC 14470 | KIT |
| 20 | *M. haemophilum* | ATCC 29548 | KIT |
| 21 | *M. intracellulare* | ATCC 13950 | KIT |
| 22 | *M. interjectum* | ATCC 51457 | KIT |
| 23 | *M. intermedium* | ATCC 51848 | KIT |
| 24 | *M. kansasii* type I-V | | Pasteur Inst. |
| 25 | *M. malmoense* | ATCC 29571 | KIT |
| 26 | *M. marinum* | ATCC 927 | KIT |
| 27 | *M. moriokaense* | ATCC 43059 | KRIBB |
| 28 | *M. mucogenicum* | ATCC 49650 | KIT |
| 29 | *M. neoaurum* | ATCC 25795 | KIT |

TABLE 1-continued

Bacterial strains used in this study

|    | Species | Strain | Source |
|----|---------|--------|--------|
| 30 | M. nonchromogenicum | ATCC 19530 | KIT |
| 31 | M. parafortuitum | ATCC 19686 | KIT |
| 32 | M. peregrinum | ATCC 14467 | KIT |
| 33 | M. phlei | ATCC 11758 | KIT |
| 34 | M. pulveris | ATCC 35154 | KRIBB |
| 35 | M. scrofulaceum | ATCC 19981 | KIT |
| 36 | M. smegmatis | ATCC 19420 | KIT |
| 37 | M. szulgai | ATCC 35799 | KIT |
| 38 | M. terrae | ATCC 15755 | KIT |
| 39 | M. thermoresistibile | ATCC 19527 | KIT |
| 40 | M. triviale | ATCC 23292 | KIT |
| 41 | M. tuberculosis H37Rv | ATCC 27294 | KIT |
| 42 | M. ulcerans | ATCC 19423 | KIT |
| 43 | M. vaccae | ATCC 15483 | KIT |
| 44 | M. xenopi | ATCC 19250 | KIT |
| 45 | N. brasiliens | ATCC 19296 | KIT |
| 46 | N. nova | ATCC 21197 | KIT |
| 47 | R. equi | ATCC 10146 | KIT |

DNA preparation.

In order to prepare a DNA sample for PCR amplification, a loopful of bacterial colony was taken from the Löwenstein-Jensen medium and resuspended in 400 µl of distilled water in a screw-cap microcentrifuge tube. The sample was then boiled for 5 min, centrifuged for 5 min to settle down cell debris, and about 10 µl of supernatant containing.

PCR amplification.

The primer set used to amplify the region of the rpoB were 5'-TCAAGGAGAAGCGCTACGA-3' (RPO5', SEQ ID NO:25) and 5'-GGATGTTGATCA GGGTCTGC-3' (RPO3', SEQ ID NO:26) resulting in about 360-bp PCR product (base number 902 to 1261 and codon number 302 to 420 based on the sequence numbers for the rpoB gene of *M. tuberculosis*, GenBank accession No. p47766). The primer sequences were selected from the region of the rpoB genes that have been previously identified from *M. tuberculosis, M. leprae*, and *M. smegmatis* (12, 13, 22). The primers were made to amplify the region between the variable region and conserved region based on the genetic information for the rpoB gene of *Escherichia coli*. As a result, PCR products included 171-bp of variable region and 189-bp of conserved region. Variable region was amplified in this experiment based on an assumption that the polymorphic nature of this region might help the clear distinction of each mycobacterial species using molecular biological techniques such as PRA and PCR-DNA hybridization. On the other hand, the region of the rpoB gene was also chosen to be flanked by highly conserved sequences, thus can be suitable for PCR amplification of the rpoB region of all mycobacterial species using the same set of PCR primers.

PCR was carried out in a final volume of 50 µl with 10 µl of DNA supernatant containing approximately 10 ng of genomic DNA, 10 pmole of each primer, 2 mM $MgCl_2$, 200 µM of deoxynucleotide triphosphates, and 1 unit of DYNAZYME® II DNA polymerase (FINNZYMES, Espoo, Finland). DNA samples were first denatured completely by incubation at 94° C. for 5 min before amplification cycle, then amplified using a cycle that includes (1) denaturation at 94° C. for 1 min, (2) primer annealing at 58° C. for 1 min, and (3) elongation at 72° C. for 1 min for 35 times using a thermocycler (model 9600, Perkin Elmer). After the last amplification cycle, the samples were incubated further at 72° C. for 7 min for complete elongation of the final PCR products. Positive and negative controls were always included in each PCR reaction. The positive control was the PCR mix with DNA of reference strain, *M. bovis,* and the negative control was the PCR mix without any DNA. After the PCR, the amplification results were visualized using 1.5% agarose gel electrophoresis and ethidium bromide staining.

Restriction fragment length polymorphism analysis.

After successful amplification, the 360-bp long PCR products were subjected to restriction enzyme digestion. Most of the time, 16 µl of PCR products (approximately 1 to 1.5 µg of DNA) were digested in a 20 µl of reaction volume using 5 units of Msp I (Boehringer Mannheim Biochemicals, Mannheim, Germany) and 2 µl of 10× reaction buffer supplied by manufacturer. Similarly, 16 µl of PCR product was digested in a 20 µl of reaction volume containing 5 units of Hae III enzyme (Takara Shuzo Co., LTD., Shiga, Japan) with the corresponding enzyme buffer. If necessary, additional enzyme digestions were carried out in a similar reaction condition. After 2 hours of incubation at 37° C., 4 µl of gel loading buffer (0.25% bromophenol blue, 40% sucrose in water) was added, and the samples were loaded into a 4% metaphore agarose gel (FMC BioProducts, Rockland, Maine). Then, enzyme digested fragments were visualized by ethidium bromide staining and UV-light.

For the interpretation of the PRA profiles generated by each species, 50-bp ladder DNA size marker (Boehringer Mannheim, Germany) and the PRA profile of *M. bovis*, which generates about 175-bp, 80-bp, 60-bp, 40-bp restriction fragments, were used as an internal size marker. Using these size markers, the sizes of the restricted fragments of each species were determined, and an algorithm was made based on this information.

Cloning and sequence analysis.

For sequence analysis, PCR products were purified by using a GENECLEAN® kit (BIO101, Vista, Calif. USA) from an agarose gel and cloned into TOPO-TA cloning vector (Invitrogen Co., Carlsbad, Calif.) by the method recommended by the manufacturer. DNA sequencing was done by the dideoxy nucleotide-chain termination method (21) using ARL automatic sequence (Pharmacia Biotechs, Uppsala, Sweden). For each clone, M13 reverse primer and T7 promoter primer were used separately to read sequences from both directions. Sequences were aligned using a multiple sequence alignment program (6).

Oligonucleotide probes used in PCR-DNA hybridization assay

Oligonucleotide probes for detecting specific mycobacterial species were designed to be 15–17 nucleotide long, and to contain 10–11 G+C content (Table 2). However, the oligonucletide probe for all the mycobactrial species (named as "Pan-TB" probe) was designed to be 20 nucleotide long. These specific oligonucleotide length and G+C content were selected, so that the hybridization conditions for each oligonucleotide to each mycobacterial DNA to be about the same.

TABLE 2

Oligonucleotide probes designed in this study to develop PCR probe hybridization assay for Mycobacterial species identification.

| Name of oligonucleotides | Sequences of oligonucleotides | Target Mycobacteria |
|---|---|---|
| PAN-MYC | GACGTCGTCGCCACCATCGA (nucteotides 108 to 127 of SEQ ID NO:1) | All mycobacterial species |
| TB | CATGTCGGCGAGCCC (nucleotides 66 to 80 of SEQ ID NO:5 | M. tuberculosis complex |
| AVIUM | CGGTGAGCCGATCACCA (nucleotides 71 to 87 of SEQ ID NO:15) | M. avium |
| INTRA | CCTGCACGCGGGCGA (nucleotides 62 to 76 of SEQ ID NO:20) | M. intracellularae |
| GORDONAE | GTCGGCGATCCGATCA (nucleotides 69 to 84 of SEQ ID NO:1) | M. gordonae |
| SZULGAI | TCTGAACGTCGGCGAG (nucleotides 61 to 76 of SEQ ID NO:12) | M. szulgai |
| KANSASII | GGCCACGATGACCGTG (nucleotides 155 to 170 of SEQ ID No:8) | M. kansasii |
| GASTRI | TCTGAACGTCGGCGAG (nucleotides 61 to 76 of SEQ ID NO:12) | M. gastri |
| FORTUITUM | CCTGAACGCCGGCCAG (nucleotides 62 to 77 of SEQ ID NO:19) | M. fortuitum<br>M. fortuitum complex |
| SCROFULACEUM | CGTACGGATGGCCAGC (nucleotides 153 to 168 of SEQ ID NO:9) | M. scrofulaceum |
| CHELONAE | TGGTGACTGCCACCACG (nucleotides 85 to 101 of SEQ ID NO:7) | M. chelonae |
| ABSCESSUS | AGGTGACCACCACCACC (nucleotides 85 to 101 of SEQ ID NO:21) | M. abscesus<br>M. terrae |
| ULCERANS/ MARINUM | GGCCAGCCCATCACC (nucleotides 72 to 86 of SEQ ID NO:10) | M. ulcerans/<br>M. marinum<br>M. genavanse/M. simiae |

PCR-dot blot hybridization.

To prepare the DNA dot blot, pre-cut (10×10 cm²) membrane (Hybond-N⁺; Ammersham) was immersed into the denaturing solution (0.4N NaOH, 25 mM EDTA; pH 8.0) for 1 min. After dripping excess amount of denaturing solution, the membrane was placed on the 3 MM paper, and 1–2 μl of PCR product was blotted on the membrane. Then, the membrane was air-dried for 5 min, rinsed with the denaturing solution for another 1 min, placed in-between two sheets of 3 MM papers, and baked for 2 hrs at 80° C. Oligonueleotide probes were labeled by using a commercially available kit for 3'-oligolabelling and detection (ECL, Ammersham Life Science). Before hybridizing with oligonucleotide probes, membrane was prehybridized at 42° C. for 30 min, and subsequently hybridized with 10 pmol of labeled oligonucleotide probes at 42° C. for 1 hr. Then, the membrane was washed twice at room temperature for 20 min, and washed twice again at 52° C. for 15 min. Subsequent procedures including antibody binding, washing and the signal detection were all carried out by the method recommended by the manufacturer.

PCR-reverse blot hybridization.

All oligonucleotide probes to be applied on the membrane were synthesized with 5' terminal amino group, which link the oligonucleotides to the BIODYNE® C membrane (Pall BioSupport, East Hills, N.Y.) by forming covalent bond with negatively charged carboxyl group fixed on the membrane. Before blotting the oligonucleotide probes, the BIODYNE® C membrane was activated by incubating in 10 ml of freshly prepared 16% (w/v) 1-ethyl-3(3-dimethylaminopropyl) carbodiimide (EDAC). After rinsed with the water, the membrane was placed on a support cushion in a clean miniblotter system (Immunetics, Inc., Cambridge, Mass.), and the residual water was removed from the slots. Then, the slots were filled with 150 μl of the diluted oligonucleotide solutions (approximate 200 pmol to 1 nmol of oligonucleotides in 150 μl of 50 mM $NaHCO_3$, pH 8.4). Subsequently, the membrane was incubated for 1 hr at room temperature, and then excess amount of oligonucleotide solution was removed from the slots by aspiration. In order to inactivate the membrane, the membrane was removed form the miniblotter using forceps, incubated in 100 mM NaOH for 10 min in a rolling bottle, and washed in 100 ml 2×SSPE/ 0.1% SDS for 5 min at 60° C. in a plastic container under gentle shaking. Before applying PCR products on the BIODYNE® C membrane, the membrane was incubated for 5 min at room temperature in 100 ml 2×SSPE/0.1% SDS.

After placing the membrane on a support cushion into the miniblotter, in such a way that the slots were perpendicular to the line pattern of the applied oligonucleotides, residual fluid was removed from the slots by aspirations. For hybridization, about 10 μl of PCR products were diluted in 150 μl of 2×SSPE/0.1% SDS and heat-denatured for 10 min at 99° C. and chilled immediately on ice. The slots were then filled with the diluted PCR products and the membrane was hybridized for 60 min at 42° C. Following hybridization, the membrane was washed in 2×SSPE/0.5% SDS for 10 min at 52° C., and incubated with 10 ml of 1:4000 diluted peroxidase labeled streptavidin conjugate in 2×SSPE/0.5% SDS for 30–60 min at 42° C. in a rolling bottle. The membrane was then washed twice in 100 ml of 2×SSPE/0.5% SDS for 10 min at 42° C. and rinsed twice with 100 ml of 2×SSPE for 5 min at room temperature. Finally for chemiluminiscent detection of hybridizing DNA, the membrane was incubated for 1–2 min in 20 ml ECL detection liquid and exposed to the x-ray film.

RESULTS

Since the genetic information for the rpoB genes of some mycobacteria are available, sequences were aligned and searched for regions, which are suitable for PRA. As a result, a set of PCR primer was selected to amplify 360-bp region of the rpoB, which contains polymorphic region flanked by conserved regins (FIG. 1. A.).

A total of 50 mycobacterial reference strains and 3 related bacterial strains that belong to the same Actinomycetes class with mycobacteria were used to amplify the 360-bp region of the rpoB gene (Table 1). The results showed the amplification of a conserved rpoB gene present in all mycobacteria and in some other bacteria such as Nocardia and Rhodococcus spp. (FIG. 1. B). Subsequently, PCR products were subjected to two sets of restriction enzyme digestion using Msp I and Hae III individually. These two enzymes were selected on the basis of the sequence information of the rpoB gene in M. tuberculosis, M. leprae, and M. smegmatis (12, 13, 22).

Figure 2A:
FIG. 2. An example of PRA results with reference strains of mycobacteria using a set of primers (RPO5' and RPO3'). Amplified DNA was digested using both (A) Msp I and (B) Hae III restriction enzymes, and run on a 4% Metaphore agarose gel. Lane M: DNA size marker (50-bp ladder), lane 1: *M. gordonae* type IV, lane 2: *M. szulgai*, lane 3: *M. kansasii* type I, lane 4: *M. gallinarum*, lane 5: *M. avium*, lane 6: *M. scrofulaceum*, lane 7: *M. asiaticum*, lane 8: *M. chelonae*, lane 9: *M. moriokaese*, lane 10: *M. phlei*, lane 11: *M. pulveris*, lane 12: *M.fortuitum* type I, lane 13: *M. austroafricanum*, lane 14: *M. smegmatis*, lane 15: *M.marinum*.
Figure 2B:

Based on this information, PCR products were subsequently subjected for RFLP analysis (FIG. 2). In short, the result of this analysis showed that RFLP profiles of PCR products from each mycobacteria species were distinctive each other. *M. kansasii* can be easily differentiated from *M. gastri* which has much in common with non-pigmented variants of *M. kansaii*. In addition, *M. abscessus*, which has been classified as a subgroup of *M. chelonae* and was not easy to be differentiated by conventional biochemical tests was also differentiated. Furthermore, for some species, such as *M. fortuitum, M. cellatum, M. gordonae* and *M. kansasii* that are known to contain several subtypes, each subtype generated distinctive restriction profiles. Therefore, it clearly indicated that this new PRA method could differentiate mycobacterial species at the species and even at the subspecies level.

Figure 3A:
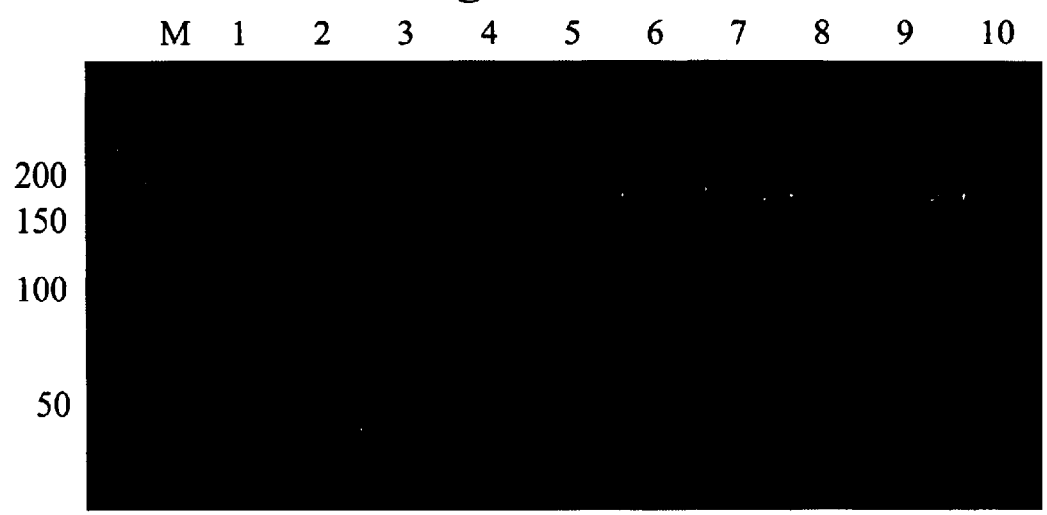
FIG. 3. PRA results with clinical isolates that have been identified by conventional methods, including microbiological and biochemical tests. PCR products were digested with Msp I enzyme and elecrophresised on 4% Metaphore agarose gel. Strains were clinical isolates of (A) *M. kansasii*, (B) *M. tuberculosis*, and (C) *M. chelonae* complex that include *M. chelonae* sub. *chelonae* and *M. chelonae* sub *abscessus*.
Figure 3B:
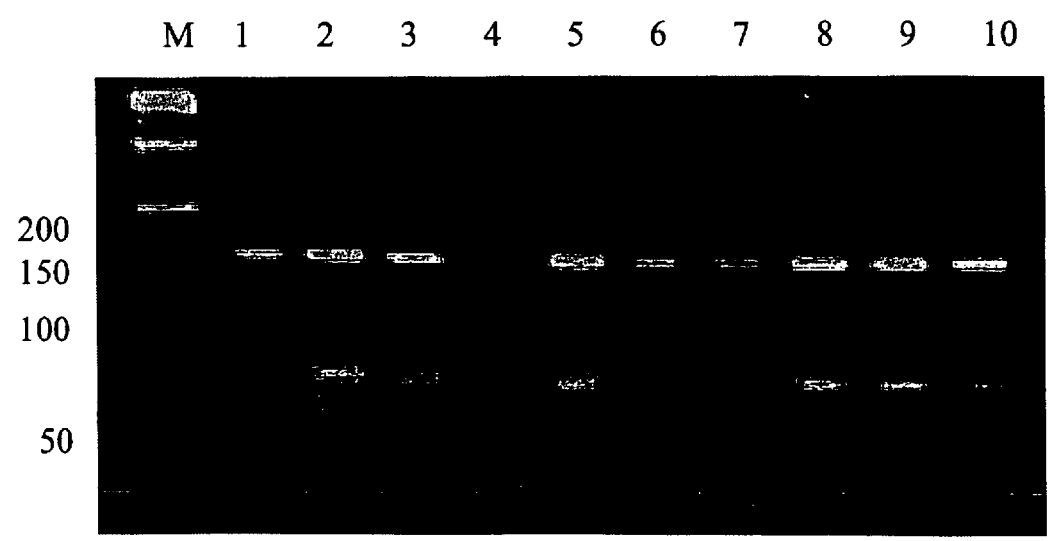
Figure 3C:
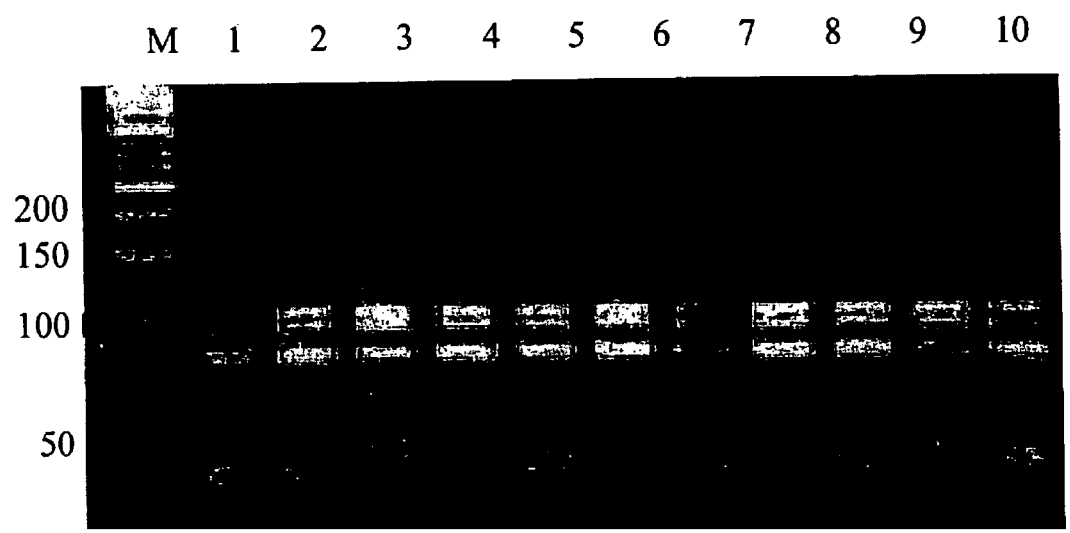

Variable RFLP profiles generated with PCR products strongly suggested to us the polymorphic nature of this rpoB region amplified by PCR in this study. Then, the next question was whether these variable RFLP profiles were species-specific or also strain-specific. If strains belonging to a certain species also show polymorphic RFLP profiles, it would be too complex to use this region for the mycobacterial species identification. Therefore, clinical isolates that have been identified on the basis of conventional tests were subjected for PRA to determine the species based on an algorithm made from this study by blind tests. The results from this experiment clearly show that there is no variation among different clinical isolates that belong to the same species (FIG. 3).

On the basis of the PRA and sequence analysis results, an algorithm was constructed (FIG. 4). In an algorithm, restriction fragments smaller than 40-bp were omitted in order to reduce the confusion with primer-dimer bands. The fragment sizes are clearly separated from each other, making interpretation of results easier. In brief, the algorithm clearly shows that most mycobacterial species and other related bacterial species can be differentiated at the subspecies level by PRA using Msp I and Hae III restriction enzymes. In fact, except for several mycobacterial species, most of species can be identified by using a single enzyme, Msp I, thus making this new method more useful for mycobacterial species identification than previously developed PRA methods.

For those strains that are not differentiated by two enzyme digestions, the third enzyme digestion was useful for differentiation. For example, even though the members of *M. tuberculosis* complex (*M. tuberculosis, M. bovis,* and *M. africanum*) were not differentiated by using Msp I and Hae III, the third enzyme Sau 3AI can differentiate *M. africanum* from other members of *M. tuberculosis* complex. In other cases, Hinc II can differetiate *M. gordonae* type I from *M. celatum* type I, and etc.

Figure 5:
FIG. 5. An example of the application of rpoB-based PRA for the species identification of mycobacterial clinical isolates in clinical laboratory. Clinical isolates were amplified using primers, RPO5' and RPO3', digested with Msp I, and run on a 4% Metaphore agarose gel. A DNA size marker (lane M: 50-bp ladder) and the PRA result of *M. bovis* was used as an internal size marker (lane 16) for each test. Using the algorithm in FIG. 3, these clinical isolates were determined to be *M. intracellulare* (lanes 1–6, 8, 9, 11–15), *M. gordonae* type II (lane 7), and *M. abscess* (lane 10).

Subsequently, a substantial number of clinical isolates that have been identified on the basis of conventional tests were subjected for PRA (Table 3). In this experiment, a total of 260 clinical isolates were analyzed including *M. tuberculosis M. avium, M. intracellulare, M. fortuitum, M. chelonae, M. abscessus, M. terrae M. gordonae, M. szulgai,* etc. For the easy interpretation of the PRA profiles generated by each clinical isolates, a 50-bp ladder size marker was used as a standard size marker, and the PRA profile of *M. bovis* was used as an internal size marker (FIG. 5). Results from the PRA of clinical isolates were evaluated with the help of an algorithm generated on the basis of PRA profiles of reference strains. Most of the PRA results were consistent with conventional test results, while PRA profiles of a few strains were not present in the reference algorithm. Based on the conventional tests and molecular biological sequence analysis, some of these were determined to be "*M. terrae* complex."

TABLE 3

Clinical isolates of mycobacteria subjected for the species identification using the new PRA.

| Species Tested | No. of Clinical Isolates |
|---|---|
| M. tuberculosis | 40 |
| M. avium | 40 |
| M. intracellulare | 50 |
| M. gordonae | 25 |
| M. szulgai | 10 |
| M. fortuitum | 25 |
| M. chelonae | 15 |
| M. abscessus | 15 |
| M. kansasii | 20 |
| M. terrae | 20 |
| Total | 260 |

Figure 6A:
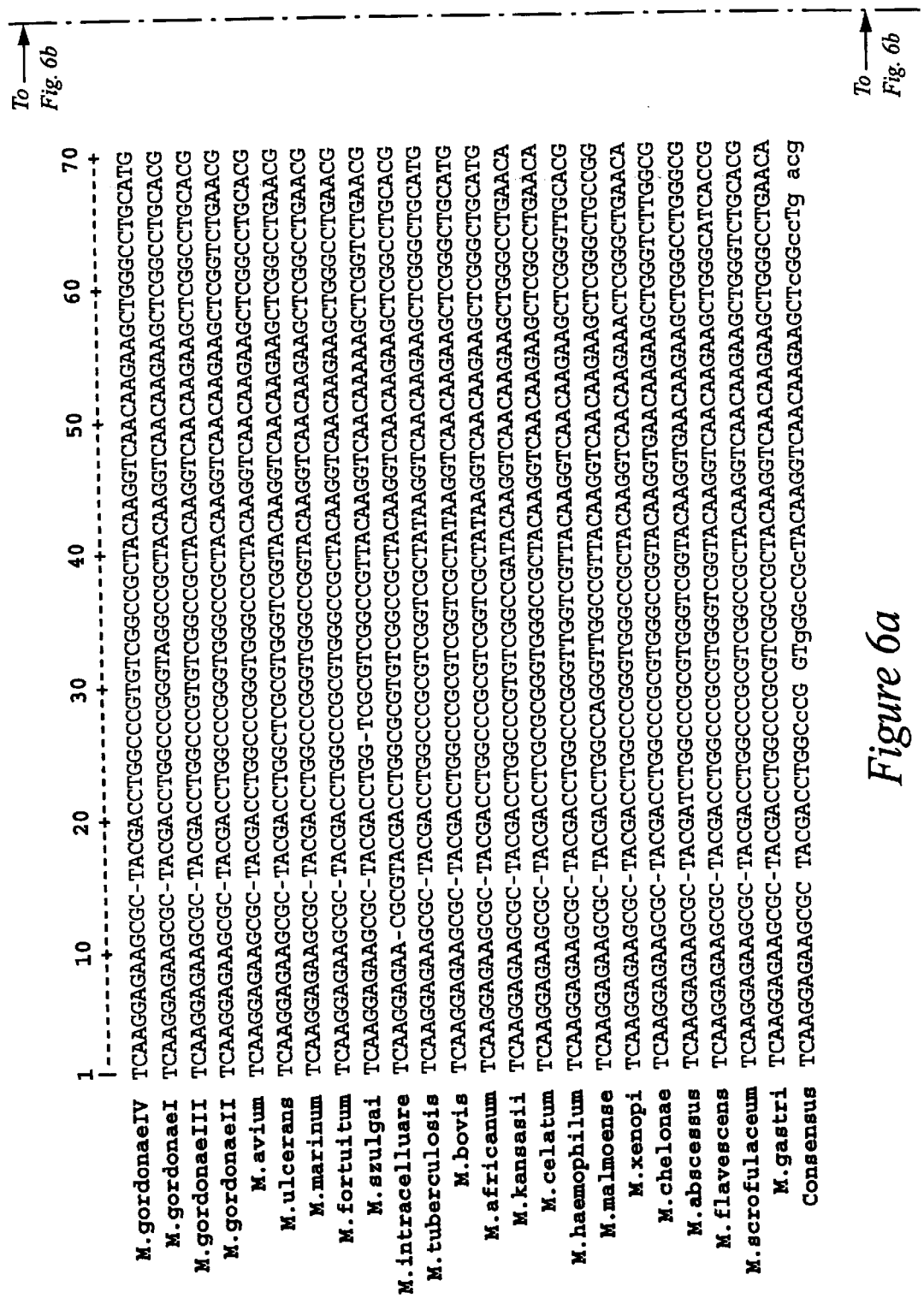
FIGS. 6A-B. Sequence alignment of the rpoB region amplified using a set of primers RPO5' and RPO3' from 35 different mycobacterial species. Sequences were aligned using multi-align program(6). Dashed lines represent nucleotide gaps.
Figure 6B:
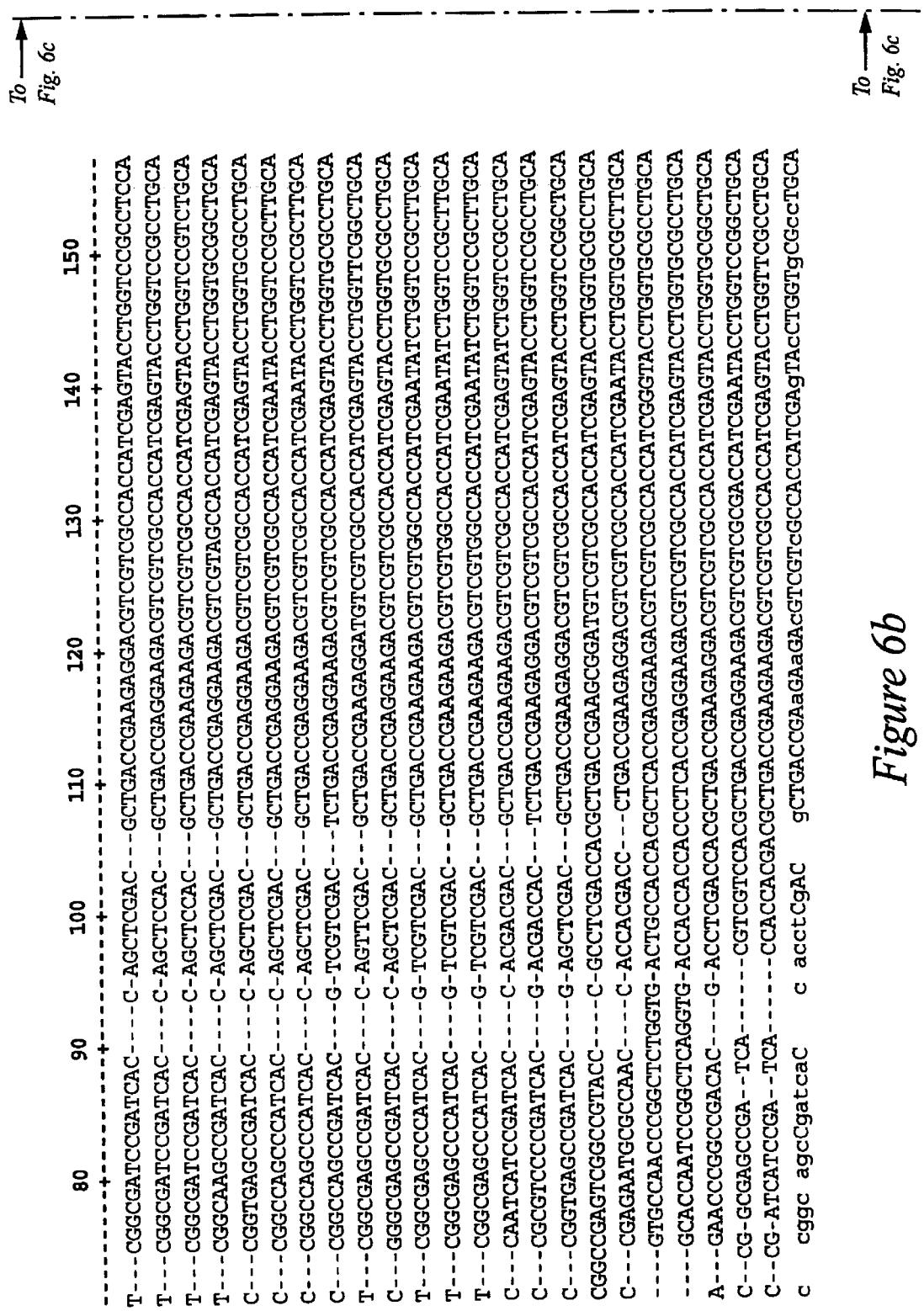

Next, we sequenced PCR amplified region of the rpoB gene derived from 30 mycobacterial species that are known to have clinical importance. Subsequently, the sequences of the amplified regions were analyzed by using a software program (6). The result of the sequence analysis clearly showed that in the region of the rpoB we amplified, highly polymorphic regions exist, which are highly species-specific (FIGS. 6A-B). This observation suggested to us that this highly polymorphic region of the rpoB can be very useful to design mycobacterial species-specific oligonucleotide probes, which can be used for developing a new PCR-dot blot hybridization technique for mycobacterial species identification. Subsequently, based on the sequence information, species-specific oligonucleotide was designed (Table 3), and each oligonucleotide was used as a probe in PCR-dot blot bybridization (FIGS. 7A-C). In this experiment, a total of 48 mycobacterial species were blotted on the membrane, and each oligonucleotide was used as a probe to detect specific mycobacterial species. In brief, the results showed that each oligonucleotide probe was shown to be highly specific to each mycobacterial species targeted, indicating the usefulness of oligonucleotides for developing probe-based mycobacterial identification systems such as PCR-dot blot hybridization and PCR-reverse blot hybridization on techniques.

Subsequently these probes were used to make a reverse-blot which can be used for the mycobacterial species identification system by using PCR-reverse blot hybridization method. The results showed that the PCR-reverse blot hybridization method employing each mycobacaterial species-specific oligonucleotide probes are very efficient system for identification of mycobacteria.

All documents cited in the specification and as references below are hereby incorporated in their entirety by reference.

REFERENCES

1. Abed, Y. C. Bollet, and, P. de Micco. 1995. Demonstration of *Mycobacterium kanasii* species heterogeneity by the amplification of the 16S–23S spacer region. J. Med Microbiol. 43:156–158.
2. Avaniss-Aghajani, E., K Jones, A. Holtzman, T. Aronson, N. Glover, M. Boian, S. Froman, and C. F. Brunk. 1996. Molecular technique for rapid identification of mycobacteria. J. Clin. Microbiol. 34:98–102.
3. Böddinghaus, B., T. Rogall, T. Flohr, H. Blöcker, and E. C. Böttger. 1990. Detection and identification of mycobacteria by amplification of rRNA. J. Clin. Microbiol. 28:1751–1759.
4. Bosne, S., and V. Lévy-Frébault. 1992. Mycobactin analysis as an aid for the identification of *Mycbacterium*

*fortuitum* and *Mycobacterium chelonae* subspecies. J. Clin. Microbiol. 30:1225–1231.

5. Butler, W. R., K. C. Jost, Jr., and J. O. Kilburn. 1991. Identification of mycobacteria by high-performance liquid chromatography. J. Clin. Microbiol. 29:2468–2472.

6. Corpet. F. 1988. Multiple sequence alignment with hierarchical clustering. Nucl. Acids. Res. 16: 10881–10890.

7. Devallois A., K. S. Goh, and N. Rastogi. 1997. Rapid identification of Mycobacteria to species level by PCR-restriction fragment length polymorphism analysis of the hsp65 gene and proposition of an algorithm to differentiate 34 mycobacterial species. J. Clin. Microlbiol. 35:2969–2973.

8. Fiss, E., F. Chebab, and G. Brooks. 1992. DNA amplification and reverse dot blot hybridization for detection and identification of mycobacteria to the species level in the clinical laboratory. J. Clin. Microbiol. 30:1220–1224.

9. Fries, J., R. Patel, W. Piessens, and D. Wirth. 1990. Genus-and species-specific DNA probes to identify mycobacteria using the polymerase chain reaction. Mol. Cell. Probes. 4:87–105.

10. Gingeras, T. R., G. Chandour, E. Wang, A. Berno, P. M. Small, F. Drobniewski, D. Alland, E. Desmond, M. Holokniy, and J. Drenkow. 1998. Simultaneous genotyping and species identification using hybridization pattern recognition analysis of generic Mycobacterium DNA arrays. Genome Res. 8:435–448.

11. Hance, A. J., B. Grandchamp, V. Lévy-Fréault, D. Lecossier, J. Rauzier, D. Bocart, and B. Gicquel. 1989. Detection and identification of mycobacteria by amplification of mycobacterial DNA. Mol. Microbiol. 3:843–849.

12. Hetherington, S. V., A. S. Watson, and C. C. Patrick. 1995. Sequence and analysis of the rpoB gene of *Mycobacterium smegmatis*. Antimicrob. Agents Chemother. 39:2164–2166.

13. Honore, N. T., S. Bergh, S. Chanteau, F. Doucet-Populaire, K. Eigimeier, T. Garnier, C. Geroges, P. Launois, T. Limpaiboon, S. Newton, K. Niang, P. Del Portillo, G. R. Ramesh, P. Reddi, P. R. Ridel, N. Sittisombut, S. Wu-Hunter, and S. T. Cole. 1993. Nucleotide sequence of the first cosmid from the *Mycobacterium leprae* genome project: structure and function of the Rif-Str regions. Mol. Microbiol. 7:207–214.

14. Hughes, M. S., R. A. Skuce, L.-A. Beck, and S. D. Neill. 1993. Identification of mycobacteria from animanls by restriction enzyme analysis and direct DNA cycle sequencing of polymerase chain reaction-amplified 16S rRNA gene sequences. j. Clin. Microbiol. 31:3216–3222.

15. Kapur, V., L.-L. Li, M. R. Hamrick, B. B. Plikaytis, T. M. Shinnick, A. Telenti, W. R. Jacobs, A. Banerjee, S. Cole, K. Y. Yuen, J. E. Clarridge, B. N. Kreiswirth, and J. M. Musser. 1995. Rapid Mycobacterium species assignment and unambiguous identification of mutations associated with antimicrobial resistance in *Mycoabcterium tuberculosis* by automated DNA sequencing. Arch. Pathol. Lab. Med. 119:131–138.

16. Kim, B.-J., S.-H. Lee, M.-A. Lyu, S.-J. Kim, G.-H. Bai, S.-J. Kim, G.-T. Chae, E.-C. Kim, C.-Y. Cha, and Y.-H. Kook. 1999. Identification of Mycobacterial species by comparative sequence analysis of the RNA polymerase gene (rpoB). J. Clin. Micro. 37:1714–1720.

17. Kirschner, P., B. Springer, U. Vogel, A. Meier, A. Wrede, M. Kiekenbeck, F.-C. Bange, and E. C. Böttger. 1993. Genotypic identification of mycobacteria by nucleic acid sequence determination; report of a 2-year experience in a clinical laboratory. J. Clin. Microbiol. 31:2882–2889.

18. Kusunoki, S., T. Ezaki, M. Tamesada, Y. Hatanaka, K. Asano, Y. Hashimoto, and E. Yabuuchi. 1991. Application of colorimetric microdilution plate hybridization for rapid genetic identification of 22 Mycobacterium species. J. Clin. Microbiol. 29:1596–1603.

19. Lévy-Frébault V., M. Daffé, K. S. Goh, M.-A. Lanéelle, C. Asselineau, and H. L. David. 1983. Identification of *Mycobacterium fortuitum* and *Mycobacterium chelonae*. J. Clin. Microbiol. 17:744–752.

20. Mabilat, C., S. Desvarenne, G. Panteix, N. Machabert, M.-H. Bernillon, G. Guardiola, and P. Cros. 1994. Routine identification of *Mycobacterium tuberculosis* complex isolates by automated hybridization. J. Clin. Microbiol.

21. Marks, J., and T. Szulga. 1965. Thin-layer chromatography of mycobacterial lipids as an aid to classification; technical procedures; *Mycobacterium fortuitum*. Tubercle 46:400–411.

22. Miller, L. P., J. T. Crawford, and T. M. Shinnick. 1994. The rpoB gene of *Mycobacterium tuberculosis*. Antimicrob. Agents Chemother. 38:805–811.

23. Musial, C., L. Tice, L. Stockman, and G. Roberts. 1988. Identification of mycobacteria from culture by using the Gen-probe rapid diagnostic system for *Mycobacterium avium* complex and *Mycobacterium tuberculosis* complex. J. Clin. Microbiol. 26:2120–2123.

24. Picardeau, M., G. Prod'hom, L. Raskine, M. P. LePennec, and V. Vincent. 1997. Genotypic characterization of five subspecies of *Mycobacterium kansasii*. J. Clin. Microbiol. 35:25–32.

25. Plikaytis, B. B., B. D. Plikaytis, M. A. Yakrus, W. R. Butler C. L. Woodley, V. A. Silcox, and T. M. Shinnick. 1992. Differentiation of slowly growing Mycobacterium species, including *Mycobacterium tuberculosis*, by gene amplification and restriction fragment length polymorphism analysis. J. Clin. Microbiol. 30:1815–1822.

26. Rogall, T., T. Flohr, and E. Bottger. 1990. Differentiation of mycobacterial species by direct sequencing of amplified DNA. J. Gen. Microbiol. 136:1915–1920.

27. Ross, B. C., K. Jackson, M. Yang, A. Sievers, and B. Dwyer. 1992. Identification of a genetically distinct subspecies of *Mycobacterium kansasii*. J. Clin. Microbiol. 30:2930–2933.

28. Shinners, D. and H. Yeager, Jr. 1999. Nontuberculous mycobacterial infection: clinical syndromes and diagnosis: overview. p341–350, In D. Schlossberg (ed.), Tuberculosis and nontuberculous mycobacterial infections, 4th ed. W. B. Saunders Co., Philadelphia Pa.

29. Shinnick, T. M. 1987. The 65-kilodalton antigen of *Mycobacterium tuberculosis*. J. Bacteriol. 169:1080–1088.

30. Shinnick, T. M., M. H. Vodkin, and J. C Williams. 1988. The *Mycobacterium tuberculosis* 65-kilodalton antigen is a heat shock protein which corresponds to common antigen and to the *Escherichia coli* GroEL protein. Infect. Immun. 56:446–451.

31. Soini, H., E. C. Böttger, and M. K. Viljanen. 1994. Identification of mycobacteria by PCR-based sequence determination of the 32-kilodalton protein gene. J. Clin. Microbiol. 32:2944–2947.

32. Springr, B., L. Stockman, K. Teschner, G. D. Roberts, and E. C. Böttger. 1996. Two-laboratory collaborative study on identification of mycobacteria: molecular versus phenotypic methods. J. Clin. Microbiol. 34:296–303.

33. Takewaki, S.-I., K. Okuzumi, I. Manabe, M. Tanimura, K. Miyamura, K.-I. Nakahara, Y. Yazaki, A. Ohkubo, and R. Nagai. 1994. Nucleotide sequence comparison of the mycobacterial dnaJ gene and PCR-restriction fragment length polymorphism analysis for identification of mycobacterial species. Int. J. Syst. Bacteriol. 44:159–166.
34. Taylor, T. B., C. Patterson, Y. Hale, and W. W. Safranek. 1997. Routine use of PCR-restriction fragment length polymorphism analysis for identification of mycobacteria growing in liquid media J. Clin. Microbiol. 35:79–85.
35. Telenti, A., F. Marchesi, M. Balz, F. Bally, E. C. Böttler, and T. Bodmer. 1993. Rapid identification of mycobacteria to the species level by polymerase chain reaction and restriction enzyme analysis. J. Clin. Microbiol. 31:175–178.
36. Tsang, A., I. Drupa, M. Goldgerg, J. McClatchy, and P. Brennan. 1983. Use of serology and thin-layer chromatography for the assembly of an authenticated collection of serovars within the *Mycobacterium avium-Mycobacterium intracellulare-Mycobacterium scrofulaceum* complex. Int. J. Syst. Bacteriol. 33:285–292
37. Vaneechoutte, M., H. D. Beenhouwer, G. Claeys, G. Verschraegen, A. D. Rouk, N. Paepe, A. Elaichouni, and F. Portaels. 1993. Identification of Mycobacterium species by using amplified ribosomal DNA restriction analysis. J. Clin. Microbiol. 31:2061–2065.

What is claimed is:

1. A method for identifying the species or subspecies of a mycobacterial strain comprising the steps of:
   a) digesting a DNA fragment which has a sequence selected from the group consisting SEQ ID NO:1 to SEQ ID NO:24 with at least one restriction enzyme selected from the group consisting of HaeIII, MspI, Sau3AI, and BstEII to obtain a first DNA fragment length polymorphism pattern;
   b) isolating a DNA fragment from the mycobacterial strain to be identified;
   c) amplifying rpoB region of the DNA fragment isolated in step (b), said amplification being performed by using a primer of SEQ ID NO:25 or SEQ ID NO:26 to produce an amplified DNA fragment;
   d) digesting the amplified DNA fragment of step c) with the at least one restriction enzyme employed in step a) to obtain a second DNA fragment length polymorphism pattern; and
   e) comparing the first DNA fragment length polymorphism pattern obtained in step a) with the second DNA fragment length polymorphism pattern obtained in step d), thereby identifying the species or subspecies of a mycobacterial strain.

2. A method of claim 1, wherein said first and second DNA fragment length polymorphism patterns are obtained by electrophoresis.

3. A method of claim 1, wherein said mycobacterial strain is selected from group consisting of *M. tuberculosis, M. avium, M. abscessus, M. flavescens, M. africanum, M. bovis, M. chelonae, M. celatum, M. fortuitum, M. gordonae, M. gestri, M. haemophilum, M. intracellulare, M. kansasii, M. malmoense, M. marinum, M. szulgai, M. terrae, M. scrofulaceum, M. ulcerans,* and *M. xenopi.*

\* \* \* \* \*

```
                              SEQUENCE LISTING

<160> NUMBER OF SEQ ID NOS: 26

<210> SEQ ID NO 1
<211> LENGTH: 208
<212> TYPE: DNA
<213> ORGANISM: Mycobacterium gordonae I

<400> SEQUENCE: 1
tcaaggagaa gcgctacgac ctggcccggg taggccgcta caaggtcaac aagaagctcg      60
gcctgcacgt cggcgatccg atcaccagct ccacgctgac cgaggaagac gtcgtcgcca     120
ccatcgagta cctggtccgc ctgcacgagg gccagcacac gatgaccgtc ccgggcggca     180
ccgaggtgcc ggttgagacc gacgacat                                       208

<210> SEQ ID NO 2
<211> LENGTH: 208
<212> TYPE: DNA
<213> ORGANISM: Mycobacterium gordonae II

<400> SEQUENCE: 2
tcaaggagaa gcgctacgac ctggcccggg tgggccgcta caaggtcaac aagaagctcg      60
gtctgaacgt cggcaagccg atcaccagct cgacgctgac cgaggaagac gtcgtagcca    120
ccatcgagta cctggtgcgg ctgcacgagg gtcagtcggc gatgacggtt cccggcggcg    180
ccgaggtgcc ggtggagacc gacgacat                                       208

<210> SEQ ID NO 3
<211> LENGTH: 208
<212> TYPE: DNA
<213> ORGANISM: Mycobacterium gordonae III

<400> SEQUENCE: 3
tcaaggagaa gcgctacgac ctggcccgtg tcggccgcta caaggtcaac aagaagctcg     60
gcctgcacgt cggcgatccg atcaccagct ccacgctgac cgaagaagac gtcgtcgcca    120
ccatcgagta cctggtccgt ctgcacgagg gtcagcacac gatgaccgtt ccgggcggca    180
ccgaggttcc ggtggagacc gacgacat                                       208

<210> SEQ ID NO 4
<211> LENGTH: 207
<212> TYPE: DNA

<213> ORGANISM: Mycobacterium gordonae IV

<400> SEQUENCE: 4
tcaaggagaa gcgctacgac ctggcccgtg tcggccgcta caaggtcaac aagaagctgg      60
gcctgcatgt cggcgatccg atcaccagct cgacgctgac cgaagaggac gtcgtcgcca    120
```

```
ccatcgagta cctggtccgc ctccacgagg gtcagcacac gatgacgttc cgggcgggac    180
cgaggttccg gtggagaccg acgacat                                        207

<210> SEQ ID NO 5
<211> LENGTH: 208
<212> TYPE: DNA
<213> ORGANISM: Mycobacterium tuberculosis

<400> SEQUENCE: 5
tcaaggagaa gcgctacgac ctggcccgcg tcggtcgcta taaggtcaac aagaagctcg    60
ggctgcatgt cggcgagccc atcacgtcgt cgacgctgac cgaagaagac gtcgtggcca    120
ccatcgaata tctggtccgc ttgcacgagg gtcagaccac gatgaccgtt ccgggcggcg    180
tcgaggtgcc ggtggaaacc gacgacat                                       208

<210> SEQ ID NO 6
<211> LENGTH: 208
<212> TYPE: DNA
<213> ORGANISM: Mycobacterium terrae

<400> SEQUENCE: 6
tcaaggagaa gcgctacgac ctggcccgcg tcggtcgcta taaggtcaac aagaagctcg    60
ggctgcatgt cggcgagccc atcacgtcgt cgacgctgac cgaagaagac gtcgtggcca    120
ccatcgaata tctggtccgc ttgcacgagg gtcagaccac gatgaccgtt ccgggcggcg    180
tcgaggtgcc ggtggaaacc gacgacat                                       208

<210> SEQ ID NO 7
<211> LENGTH: 214
<212> TYPE: DNA
<213> ORGANISM: Mycobacterium chelonae

<400> SEQUENCE: 7
tcaaggagaa gcgctacgac ctggcccgcg tgggccggta caaggtgaac aagaagctgg    60
gtcttggcgg tgccaacccg gctctggtga ctgccaccac gctcaccgag gaagacgtcg    120
tcgccaccat cgggtacctg gtgcgcctgc acgagggcca gaccacgatg accgcccccg    180
gcggcctcga ggtcccggtc gaggtcgacg acat                                214

<210> SEQ ID NO 8
<211> LENGTH: 208
<212> TYPE: DNA
<213> ORGANISM: Mycobacterium kansasii

<400> SEQUENCE: 8
tcaaggagaa gcgctacgac ctggcccgtg tcggccgata caaggtcaac aagaagctgg    60
gcctgaacac caatcatccg atcaccacga cgacgctgac cgaagaagac gtcgtcgcca    120
ccatcgagta tctggtccgc ctgcacgagg gccaggccac gatgaccgtg ccgggcgggg    180
tcgaggtgcc ggtggaaacc gacgacat                                       208

<210> SEQ ID NO 9
<211> LENGTH: 223
<212> TYPE: DNA
<213> ORGANISM: Mycobacterium scrofulaceum

<400> SEQUENCE: 9
tcaaggagaa gcgctacgac ctggcccgcg tcggccgcta caaggtcaac aagaagctgg    60
```

```
gtctgcacgc cggcgagccg atcacgtcgt ccacgctgac cgaggaagac gtcgtcgcga    120
ccatcgaata cctggtccgg ctgcaccacg cccgtacgga tggccagccc gccgtcatga    180
ctgtccccgg cggcatcgag gtgccggtgg agaccgacga cat                      223
```

<210> SEQ ID NO 10
<211> LENGTH: 208
<212> TYPE: DNA
<213> ORGANISM: Mycobacterium ulcerans

<400> SEQUENCE: 10

```
tcaaggagaa gcgctacgac ctggctcgcg tgggtcggta caaggtcaac aagaagctcg     60
gcctgaacgc cggccagccc atcaccagct cgacgctgac cgaggaagac gtcgtcgcca    120
ccatcgaata cctggtccgc ttgcacgagg gccagaccgc gatgaccgct ccgggcggtg    180
tcgaggtgcc ggtcgagacc gacgacat                                       208
```

<210> SEQ ID NO 11
<211> LENGTH: 208
<212> TYPE: DNA
<213> ORGANISM: Mycobacterium marinum

<400> SEQUENCE: 11

```
tcaaggagaa gcgctacgac ctggcccggg tgggccggta caaggtcaac aagaagctcg     60
gcctgaacgc cggccagccc atcaccagct cgacgctgac cgaggaagac gtcgtcgcca    120
ccatcgaata cctggtccgc ttgcacgagg gccagaccgc gatgaccgct ccgggcggtg    180
tcgaggtgcc ggtcgagacc gacgacat                                       208
```

<210> SEQ ID NO 12
<211> LENGTH: 207
<212> TYPE: DNA
<213> ORGANISM: Mycobacterium szulgai

<400> SEQUENCE: 12

```
tcaaggagaa gcgctacgac ctggtcgcgt cggccgttac aaggtcaaca aaaagctcgg     60
tctgaacgtc ggcgagccga tcaccagttc gacgctgacc gaagaggatg tcgtcgccac    120
catcgagtac ctggttcggc tgcacgaggg ccagaccacg atgaccgttc ccggcggcac    180
cgaggtgccg gtggagaccg acgacat                                        207
```

<210> SEQ ID NO 13
<211> LENGTH: 223
<212> TYPE: DNA
<213> ORGANISM: Mycobacterium gastri

<400> SEQUENCE: 13

```
tcaaggagaa gcgctacgac ctggcccgcg tcggccgcta caaggtcaac aagaagctgg     60
gcctgaacac cgatcatccg atcaccacca cgacgctgac cgaagaagac gtcgtcgcca    120
ccatcgagta cctggttcgc ctgcaccacg cctctcaggg tggccaggcc ccgttatga    180 ctgtccccgg cggggtcgag gtgccggtgg aaaccgacga cat                      223
```

<210> SEQ ID NO 14
<211> LENGTH: 214
<212> TYPE: DNA
<213> ORGANISM: Mycobacterium malmoense

<400> SEQUENCE: 14

```
tcaaggagaa gcgctacgac ctggccaggg ttggccgtta caaggtcaac aagaagctcg     60
```

-continued

```
ggctgccggc ggccgagtcg gccgtacccg cctcgaccac gctgaccgaa gcggatgtcg      120
tcgccaccat cgagtacctg gtgcgcctgc acgagggcca ggcaacgatg acggttcccg      180
gcggcgtcga ggtgccggtg gagaccgacg acat                                 214

<210> SEQ ID NO 15
<211> LENGTH: 208
<212> TYPE: DNA
<213> ORGANISM: Mycobacterium avium

<400> SEQUENCE: 15
tcaaggagaa gcgctacgac ctggcccggg tgggccgcta caaggtcaac aagaagctcg      60
gcctgcacgc cggtgagccg atcaccagct cgacgctgac cgaggaagac gtcgtcgcca     120
ccatcgagta cctggtgcgc ctgcacgagg gtcagcccac gatgaccgtc cccggcggca     180
tcgaggtgcc ggtggagacc gacgacat                                       208

<210> SEQ ID NO 16
<211> LENGTH: 208
<212> TYPE: DNA
<213> ORGANISM: Mycobacterium bovis

<400> SEQUENCE: 16
tcaaggagaa gcgctacgac ctggcccgcg tcggtcgcta taaggtcaac aagaagctcg      60
ggctgcatgt cggcgagccc atcacgtcgt cgacgctgac cgaagaagac gtcgtggcca     120
ccatcgaata tctggtccgc ttgcacgagg gtcagaccac gatgaccgtt ccgggcggcg     180
tcgaggtgcc ggtggaaacc gacgacat                                       208

<210> SEQ ID NO 17
<211> LENGTH: 208
<212> TYPE: DNA
<213> ORGANISM: Mycobacterium celatum

<400> SEQUENCE: 17
tcaaggagaa gcgctacgac ctcgcgcggg tgggccgcta caaggtcaac aagaagctcg      60
gcctgaacac cgcgtccccg atcacgacga ccactctgac cgaagaggac gtcgtcgcca     120
ccatcgagta cctggtccgc ctgcacgagg gccacaccac gatgaccgtc ccgggcggag     180
tcgaggtgcc ggtggaaacc gacgacat                                       208

<210> SEQ ID NO 18
<211> LENGTH: 211
<212> TYPE: DNA
<213> ORGANISM: Mycobacterium flavescens

<400> SEQUENCE: 18
tcaaggagaa gcgctacgac ctggcccgcg tgggtcggta caaggtcaac aagaagctgg      60
gcatcaccga gaacccggcc gacacgacct cgaccacgct gaccgaagag gacgtcgtcg     120
ccaccatcga gtacctggtg cggctgcatc agggcgacaa gacgatgacc gtcccgggtg     180
gagtcgaggt gcccgtcgag gtcgacgaca t                                   211

<210> SEQ ID NO 19
<211> LENGTH: 208
<212> TYPE: DNA
<213> ORGANISM: Mycobacterium fortuitum

<400> SEQUENCE: 19
```

```
tcaaggagaa gcgctacgac ctggcccgcg tgggccgcta caaggtcaac aagaagctgg      60
gcctgaacgc cggccagccg atcacgtcgt cgactctgac cgaggaagac gtcgtcgcca    120
ccatcgagta cctggtgcgc ctgcacgagg ccagaccac gatgaccgtc cccggcggcg     180
tcgaggtccc ggtcgaggtg gacgacat                                        208

<210> SEQ ID NO 20
<211> LENGTH: 205
<212> TYPE: DNA
<213> ORGANISM: Mycobacterium intracellulare

<400> SEQUENCE: 20
tcaaggagaa cgcgtacgac ctggcgcgtg tcggccgcta caaggtcaac aagaagctcg     60
gcctgcacgc gggcgagccg atcaccagct cgacgctgac cgaggaagac gtcgtcgcca    120
ccatcgagta cctggtgcgc ctgcacgagg ccagcccac gatgaccgtc cccggcatcg     180
aggtgccggt ggagaccgac gacat                                           205

<210> SEQ ID NO 21
<211> LENGTH: 214
<212> TYPE: DNA
<213> ORGANISM: Mycobacterium abscessus

<400> SEQUENCE: 21
tcaaggagaa gcgctacgat ctggcccgcg tgggtcggta caaggtgaac aagaagctgg     60
gcctgggcgg caccaatccg gctcaggtga ccaccaccac cctcaccgag gaagacgtcg    120
tcgccaccat cgagtacctg gtgcgcctgc acgagggcca gaccacgatg accgcccccg   180
gcggcgtcga ggtgccggtg gatgtggacg acat                                 214

<210> SEQ ID NO 22
<211> LENGTH: 208
<212> TYPE: DNA
<213> ORGANISM: Mycobacterium africanum

<400> SEQUENCE: 22
tcaaggagaa gcgctacgac ctggcccgcg tcggtcgcta taaggtcaac aagaagctcg     60
ggctgcatgt cggcgagccc atcacgtcgt cgacgctgac cgaagaagac gtcgtggcca    120
ccatcgaata tctggtccgc ttgcacgagg gtcagaccac gatgatcgtt ccgggcggcg    180
tcgaggtgcc ggtggaaacc gacgacat                                        208

<210> SEQ ID NO 23
<211> LENGTH: 208
<212> TYPE: DNA
<213> ORGANISM: Mycobacterium haemophilum

<400> SEQUENCE: 23
tcaaggagaa gcgctacgac ctggcccggg ttggtcgtta caaggtcaac aagaagctcg     60
ggttgcacgc cggtgagccg atcacgagct cgacgctgac cgaagaggac gtcgtcgcca    120
ccatcgagta cctggtccgg ctgcatgagg gtcagtcgac gatgaccgtt ccaggtggcg    180
tcgaggtgcc agtggatact gacgacat                                        208

<210> SEQ ID NO 24
<211> LENGTH: 208
<212> TYPE: DNA
<213> ORGANISM: Mycobacterium xenopi

<400> SEQUENCE: 24
```

```
tcaaggagaa gcgctacgac ctggcccggg tgggccgcta caaggtcaac aagaaactcg        60
ggctgaacac cgagaatgcg ccaaccacca cgaccctgac cgaagaggac gtcgtcgcca       120
ccatcgaata cctggtgcgc ttgcacgagg ggcacgccac gatgaaggtc cccggtggcg       180
tcgaggtgcc ggtggagacc gacgacat                                          208

<210> SEQ ID NO 25
<211> LENGTH: 19
<212> TYPE: DNA
<213> ORGANISM: Artificial Sequence
<220> FEATURE:
<223> OTHER INFORMATION: Chemically synthesized PCR amplication primer
      for amplifying the rpoB region of Microbacterial species

<400> SEQUENCE: 25
tcaaggagaa gcgctacga                                                     19

<210> SEQ ID NO 26
<211> LENGTH: 20
<212> TYPE: DNA
<213> ORGANISM: Artificial Sequence
<220> FEATURE:
<223> OTHER INFORMATION: Chemically synthesized PCR amplication primer
      for amplifying the rpoB region of Microbacterial species

<400> SEQUENCE: 26
ggatgttgat cagggtctgc                                                    20
```